(12) United States Patent
Gunaratne et al.

(10) Patent No.: US 8,765,707 B2
(45) Date of Patent: Jul. 1, 2014

(54) MICRORNA-140-5P AS A TUMOR SUPPRESSOR AND SENSITIZING AGENT FOR CHEMOTHERAPY

(75) Inventors: Preethi H. Gunaratne, Houston, TX (US); Jason M. Shohet, Pearland, TX (US)

(73) Assignees: University of Houston System, Houston, TX (US); Baylor College of Medicine, Houston, TX (US)

( * ) Notice: Subject to any disclaimer, the term of this patent is extended or adjusted under 35 U.S.C. 154(b) by 0 days.

(21) Appl. No.: 13/453,553

(22) Filed: Apr. 23, 2012

(65) Prior Publication Data

US 2012/0269883 A1    Oct. 25, 2012

Related U.S. Application Data

(60) Provisional application No. 61/517,633, filed on Apr. 22, 2011.

(51) Int. Cl.
*C12N 15/11*    (2006.01)

(52) U.S. Cl.
USPC ........................................ 514/44 A

(58) Field of Classification Search
USPC ............................. 514/44 A, 44 R
See application file for complete search history.

(56) References Cited

U.S. PATENT DOCUMENTS

| | | | |
|---|---|---|---|
| 7,955,848 B2 * | 6/2011 | Dmitrovsky et al. | ......... 435/325 |
| 2008/0171715 A1 | 7/2008 | Brown et al. | |
| 2009/0186348 A1 | 7/2009 | Huibregtse et al. | |
| 2010/0179213 A1 | 7/2010 | Patrawala et al. | |
| 2010/0249213 A1 | 9/2010 | Croce | |

FOREIGN PATENT DOCUMENTS

WO    2010108192 A1    9/2010

OTHER PUBLICATIONS

Motoyama et al., Int. J. Oncol. (2009); 34:1069-1075.*
Schaefer et al., Int. J. Cancer (2010); 126:1166-1176.*

* cited by examiner

*Primary Examiner* — Jon E Angell
(74) *Attorney, Agent, or Firm* — Benjamin Aaron Adler

(57) ABSTRACT

The present invention provides a method of improving a therapeutic response to a cancer treatment, in a subject, the method comprising administering an effective amount of an agent that enhances the expression of microRNA-140-5p or an agent that mimics the effects of microRNA-140-5p. Further provided is a method of treating a cancer in a subject in need of such treatment comprising the step of administering an effective amount of a microRNA-140-5p or an agent that enhances the expression of microRNA-140-5p.

26 Claims, 4 Drawing Sheets

MICRORNA-140-5P AS A TUMOR SUPPRESSOR AND SENSITIZING AGENT FOR CHEMOTHERAPY

CROSS-REFERENCE TO RELATED APPLICATIONS

This non-provisional application claims benefit of priority under 35 U.S.C. §119(e) of provisional application U.S. Ser. No. 61/517,633, filed Apr. 22, 2011, now abandoned, the entirety of which is hereby incorporated by reference.

BACKGROUND OF THE INVENTION

1. Field of the Invention

The present invention relates generally to the fields of microRNA molecular biology and cancer. More specifically, the invention relates to the use of microRNA-140-5p as tumor suppressors able to significantly suppress cell proliferation, increase apoptosis, suppress tumor growth and increase sensitivity of chemotherapeutic drugs.

2. Description of the Related Art

RNA interference refers to the process of sequence-specific post-transcriptional gene silencing in animals mediated by short interfering RNAs (siRNAs) (1). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (2). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA.

The presence of dsRNA in cells triggers the RNAi response through a mechanism that has yet to be fully characterized. The presence of long dsRNAs in cells stimulates the activity of a ribonuclease III enzyme referred to as dicer. Dicer is involved in the processing of the dsRNA into short pieces of dsRNA known as short interfering RNAs (siRNAs) (3). Short interfering RNAs derived from dicer activity are typically about 21 to about 23 nucleotides in length and comprise about 19 base pair duplexes (4). Dicer has also been implicated in the excision of 21- and 22-nucleotide small temporal RNAs (stRNAs) from precursor RNA of conserved structure that are implicated in translational control (5). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex (4). In addition, RNA interference can also involve small RNA (e.g., microRNA, or miRNA) mediated gene silencing, presumably through cellular mechanisms that regulate chromatin structure and thereby prevent transcription of target gene sequences (7-9).

As such, miRNA molecules of the invention can be used to mediate gene silencing via interaction with RNA transcripts or alternately by interaction with particular gene sequences, wherein such interaction results in gene silencing either at the transcriptional or post-transcriptional level. RNAi has been studied in a variety of systems. Fire et al. (1) were the first to observe RNAi in *C. elegans*. Wianny and Goetz (10) describe RNAi mediated by dsRNA in mouse embryos. Hammond et al. (11) describe RNAi in *Drosophila* cells transfected with dsRNA. Elbashir et al. (4) describe RNAi induced by introduction of duplexes of synthetic 21-nucleotide RNAs in cultured mammalian cells including human embryonic kidney and HeLa cells.

Small RNAs play an important role in controlling gene expression. Regulation of many developmental processes is controlled by small RNAs. It is now possible to engineer changes in gene expression of plant genes by using transgenic constructs which produce small RNAs in the plant. Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited. It is thought that sequence complementarity between small RNAs and their RNA targets helps to determine which mechanism, RNA cleavage or translational inhibition, is employed. It is believed that siRNAs, which are perfectly complementary with their targets, work by RNA cleavage. Some miRNAs have perfect or near-perfect complementarity with their targets, and RNA cleavage has been demonstrated for at least a few of these miRNAs. Other miRNAs have several mismatches with their targets, and apparently inhibit their targets at the translational level.

Without being held to a particular theory on the mechanism of action, a general rule is emerging that perfect or near-perfect complementarity favors RNA cleavage, especially within the first ten nucleotides (counting from the 5' end of the miRNA), whereas translational inhibition is favored when the miRNA/target duplex contains many mismatches. The apparent exception to this is microRNA-172 (miR172) in plants. One of the targets of miR172 is APETALA2 (AP2), and although miR172 shares near-perfect complementarity with AP2 it appears to cause translational inhibition of AP2 rather than RNA cleavage. MicroRNAs (miRNAs) are noncoding RNAs of about 19 to about 24 nucleotides (nt) in length that have been identified in both animals and plants (12-19). They are processed from longer precursor transcripts that range in size from approximately 70 to 200 nt, and these precursor transcripts have the ability to form stable hairpin structures. In animals, the enzyme involved in processing miRNA precursors is called Dicer, an RNAse III-like protein (5, 20-21). Plants also have a Dicer-like enzyme, DCL1, previously named CARPEL FACTORY/SHORT INTEGUMENTS1/SUSPENSOR1, and recent evidence indicates that it, like Dicer, is involved in processing the hairpin precursors to generate mature miRNAs (18-19).

Furthermore, it is becoming clear from recent work that at least some miRNA hairpin precursors originate as longer polyadenylated transcripts, and several different miRNAs and associated hairpins can be present in a single transcript (12, 22). Recent work has also examined the selection of the miRNA strand from the dsRNA product arising from processing of the hairpin by DICER (23). It appears that the stability, i.e. G:C vs. A:U content and/or mismatches, of the two ends of the processed dsRNA affects the strand selection, with the low stability end being easier to unwind by a helicase activity. The 5' end strand at the low stability end is incorporated into the RISC complex, while the other strand is degraded.

In animals, there is direct evidence indicating a role for specific miRNAs in development. The lin-4 and let-7 miRNAs in *C. elegans* have been found to control temporal development, based on the phenotypes generated when the genes producing the lin-4 and let-7 miRNAs are mutated (24-25). In addition, both miRNAs display a temporal expression pattern consistent with their roles in developmental timing. Other animal miRNAs display developmentally regulated patterns of expression, both temporal and tissue-specific (12-15), leading to the hypothesis that miRNAs may, in many cases, be involved in the regulation of important developmental processes. Likewise, in plants, the differential expression patterns of many miRNAs suggests a role in development (16, 18-19), which has now been shown (26).

MicroRNAs appear to regulate target genes by binding to complementary sequences located in the transcripts produced by these genes. In the case of lin-4 and let-7, the target sites are located in the 3' UTRs of the target mRNAs (24-25, 27-28), and there are several mismatches between the lin-4 and let-7 miRNAs and their target sites. Binding of the lin-4 or let-7 miRNA appears to cause downregulation of steady-state levels of the protein encoded by the target mRNA without affecting the transcript itself (29). On the other hand, recent evidence suggests that miRNAs can, in some cases, cause specific RNA cleavage of the target transcript within the target site, and this cleavage step appears to require 100% complementarity between the miRNA and the target transcript (16, 30), especially within the first ten nucleotides, counting from the 5' end of the miRNA).

It seems likely that miRNAs can enter at least two pathways of target gene regulation. Protein downregulation when target complementarity is <100%, and RNA cleavage when target complementarity is 100%. MicroRNAs entering the RNA cleavage pathway are analogous to the 21-25 nt short interfering RNAs (siRNAs) generated during RNA interference (RNAi) in animals and posttranscriptional gene silencing (PTGS) in plants (11, 31-33), and likely are incorporated into an RNA-induced silencing complex (RISC) that is similar or identical to that seen for RNAi.

Identifying the targets of miRNAs with bioinformatics has not been successful in animals, and this is probably due to the fact that animal miRNAs have a low degree of complementarity with their targets. On the other hand, bioinformatic approaches have been successfully used to predict targets for plant miRNAs (16, 18, 34), and thus it appears that plant miRNAs have higher overall complementarity with their putative targets than do animal miRNAs. Most of these predicted target transcripts of plant miRNAs encode members of transcription factor families implicated in plant developmental patterning or cell differentiation. Nonetheless, biological function has not been directly demonstrated for any plant miRNA. Although Llave et al. (16) have shown that a transcript for a SCARECROW-like transcription factor is a target of the *Arabidopsis* miRNA mir171, these studies were performed in a heterologous species and no plant phenotype associated with mir171 was reported.

General categories of sequences of interest for the invention described include, for example, those genes involved in regulating oncogenic processes that are responsible for the initiation, progression or maintenance of increased cell proliferation and/or decreased cell death that are direct or indirect targets of tumor suppressor microRNAs. Target sequences further include coding regions and non-coding regions such as promoters, enhancers, terminators, introns and the like, which may be modified in order to alter the expression of a gene of interest. For example, an intron sequence can be added to the 5' region to increase the amount of mature message that accumulates (35-36).

In the current invention microRNAs are small-22 nucleotide non-coding RNAs that can bind protein coding mRNAs through complimentary base pairing to mediate mRNA decay or translational repression. Because a single microRNA can bind and silence hundreds of genes across diverse signaling pathways, there is a recognized need in the art to develop microRNAs as powerful therapeutic agents to silence entire disease networks.

The prior art is deficient in the use of the microRNA-140-5p to, inter alia, significantly enhance sensitivity to chemotherapeutic drug as well as provide an alternative or complement to small molecule inhibitor treatment for neuroblastoma and other cancers.

SUMMARY OF THE INVENTION

The present invention is directed to the use of the microRNA-140-5p and microRNA-140-5p microRNA family to, inter alia, significantly enhance sensitivity to chemotherapeutic drugs or other therapies as well as provide an alternative or complement to small molecule inhibitor treatment for ovarian and other cancers when presented in the form of pri-miRNA, pre-miRNA, mature miRNA or fragments of variants thereof that retain the biological activity of the mature miRNA and DNA encoding a pri-miRNA, pre-miRNA, mature miRNA, fragments or variants thereof, or regulatory elements of the miRNA.

Thus, the present invention is directed to a method of improving a therapeutic response to a cancer treatment in a subject, the method comprising administering an effective amount of a microRNA-140-5p or an agent that mimic the effects or enhance expression of microRNA-140-5p. Representative agents that mimic the effects or enhance expression of microRNA-140-5p include but are not limited to double-stranded microRNA 140-5p mimics and oligonucleotide based pre-microRNA-140-5p drugs.

Representative cancers include but are not limited to neuroblastoma, lung cancer, pancreatic cancer, skin cancer, hematological neoplasms, breast cancer, brain cancer, colon cancer, follicular lymphoma, bladder cancer, cervical cancer, endometrial cancer, esophageal cancer, gastric cancer, head and neck cancer, multiple myeloma, liver cancer, lymphomas, oral cancer, osteosarcomas, ovarian cancer, uterine leiomyosarcoma, uterine leiomyomas, endometriomas, endometriosis, uterine papillary serous carcinomas, prostate cancer, testicular cancer and thyroid cancer. In a preferred embodiment, the cancer is neuroblastoma. Representative therapeutic responses include but are not limited to treating with radiation, carboplatin, cisplatin, paclitaxel, an alkylating agent, an antimetabolite, an antitumor antibiotic, and a DNA topoisomerase inhibitor.

The present invention also is directed to a kit for determining a chemotherapy response in a patient with a cancer. The kit comprises an oligonucleotide complementary to microRNA-140-5p and, optionally, reagents for the formation of the hybridization between the oligonucleotide and the microRNA-140-5p. In one aspect, the microRNA-140-5p may be detectably labeled. A person with ordinary skill in this art would recognize that, in this kit, the microRNA-140-5p could be attached to a solid surface. For example, the microRNA-140-5p could be a member or component of a nucleic acid array. A representative example of a nucleic acid array is a micro-array.

The present invention is directed further to a pharmaceutical composition for improving a tumor response to chemotherapy, the composition comprising an effective amount of microRNA-140-5p or an agent that enhances the expression of microRNA-140-5p or mimics the actions of microRNA-140-5p. The pharmaceutical composition may be delivered on a nanoliposomal vector, gold or other nanoparticle carriers or viral vectors with and without genes such as p53.

The present invention is directed further still to a method of treating a cancer in a subject in need of such treatment comprising the step of administering an effective amount of a microRNA-140-5p or an agent that enhances the expression of microRNA-140-5p or mimics the actions of microRNA-140-5p. Representative examples of an agent that enhances the expression of microRNA-140-5p or mimics the actions of microRNA-140-5p include double-stranded miRNA mimics, and oligonucleotide based pre-microRNA-140-5p drugs. The microRNA-140-5p mimics and/or drugs can be delivered on liposomal, gold or other nanoparticle carriers, or nanoliposomal vectors into human patients. Representative examples of cancer which may be treated using this method include but are not limited to those cancers as described herein. In a preferred aspect, the cancer is neuroblastoma.

The present invention is directed a related method further that further comprises treating the subject with radiation, carboplatin, cisplatin, paclitaxel, an alkylating agent, an antimetabolite, an antitumor antibiotic and a DNA topoisomerase inhibitor. A person having ordinary skill in this art would readily recognize that the microRNA-140-5p, agent that enhances the expression of microRNA-140-5p or mimics the actions of microRNA-140-5p may be administered as a nucleic acid construct encoding an artificial miRNA presented as a double-stranded RNA, a precursor hairpin, a primary miRNA in single straded RNA form, encoded in a DNA vector delivered in a suitable pharmaceutical carrier. Representative examples of a pharmaceutical carrier which may be used in this method include but are not limited to a virus, a liposome, a polymer and a nanoparticle carrier. The microRNA-140-5p may be administered as a nanoparticle, a liposome, a vector or a polymer. Representative examples of vector which may be used in this method include but are not limited to a plasmid, a cosmid, a phagemid and a virus.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

DESCRIPTION OF THE PREFERRED EMBODIMENTS

Figure 1:
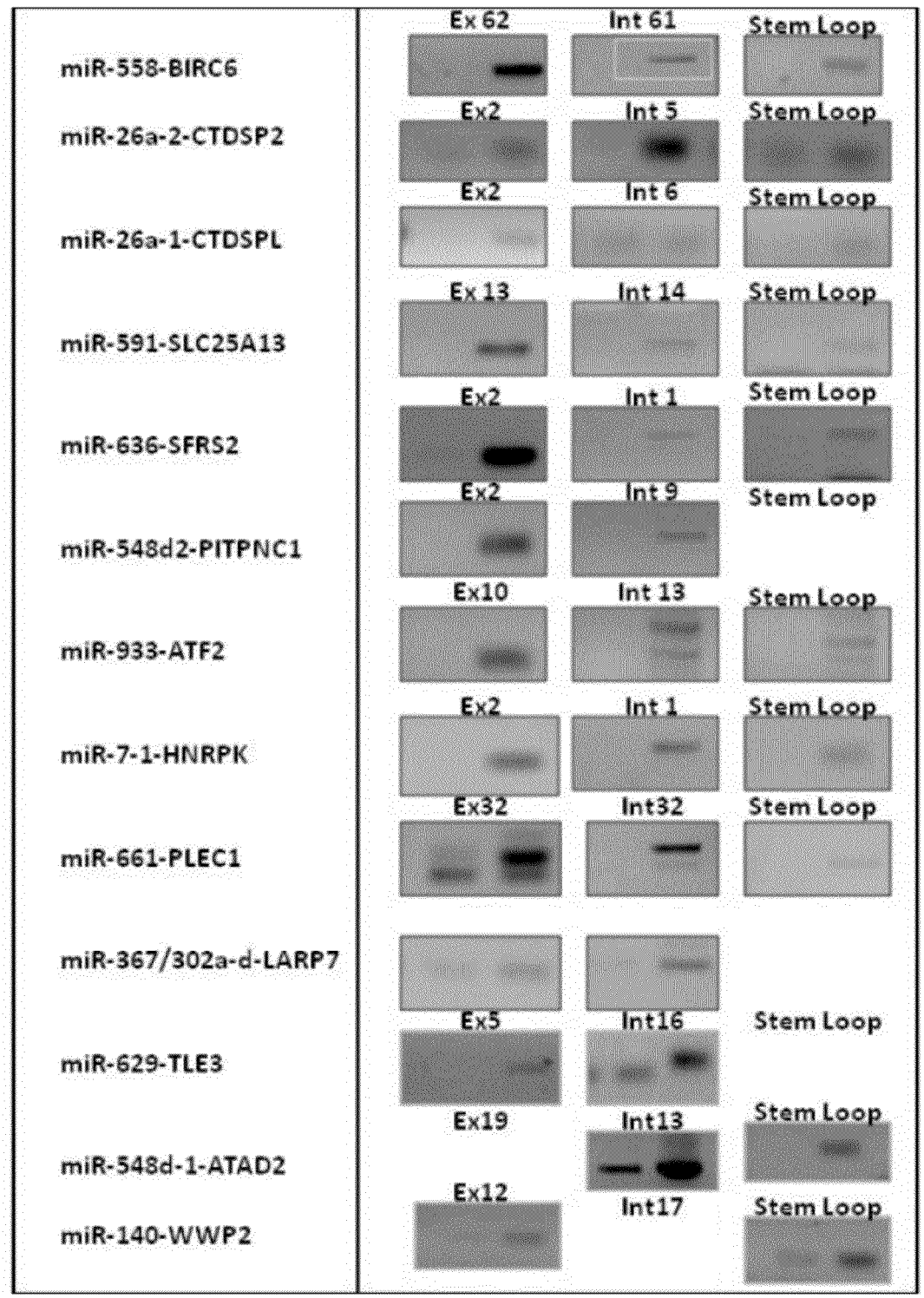
FIG. 1 shows that miR-140-5p is identified as a tumor suppressor of neuroblastoma that is repressed under conditions of high levels of MYCN.

As used herein, the term "a" or "an", when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, method steps, and/or methods of the invention. It is contemplated that any device, compound, composition, or method described herein can be implemented with respect to any other device, compound, composition, or method described herein.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the terms "microRNA-140-5p", "miR-140-5p" or "miRNA-140-5p" are used interchangeably As used herein, the term "subject" refers to any recipient of any agent suitable to enhance expression of or that mimics the effects of microRNA-140-5p as described herein.

The present invention relates to the design, synthesis, construction, composition, characterization and use of a therapeutic microRNAs and methods useful in treating cancer using such microRNAs. More specifically, the invention discloses that artificial microRNA-140-5p is a potent tumor suppressor able to significantly suppress cell proliferation, increase apoptosis, suppress tumor growth and increase sensitivity of chemotherapeutic drugs when presented in the form of pri-miRNA, pre-miRNA, mature miRNA or fragments of variants thereof that retain the biological activity of the mature miRNA and DNA encoding a pri-miRNA, pre-miRNA, mature miRNA, fragments or variants thereof, or regulatory elements of the miRNA.

One preferred embodiment of the invention discloses the use of a nucleic acid construct encoding an artificial miRNA presented as a double-stranded RNA or precursor a hairpin or a primary miRNA in the single straded RNA form or encoded in a DNA vector delivered in a suitable pharmaceutical carrier, to be used for inhibiting the expression of all oncogenes and regulators of oncogenes containing a miR-140-5p complementary site (LCS). The pharmaceutical carrier includes, but is not limited to, a virus, a liposome, or a polymer, and any combination thereof.

Another preferred embodiment of the present invention discloses the composition, methods and use of a nucleic acid construct encoding an artificial miRNA presented as a double-stranded RNA or precursor a hairpin or a primary miRNA in the single stranded RNA form or encoded in a DNA vector delivered in a suitable pharmaceutical carrier, to be used for inhibiting the expression of all oncogenes and regulators of oncogenes containing a miR-140-5p complementary site (LCS), wherein the miR-140-5p is delivered in multiple ways, to include but not limited to, as a mature miRNA by itself, or as a gene is encoded by a nucleic acid, or as a precursor hairpin by itself or conjugated to nanoparticles of metal or liposomal origin, or conjugated to nanoparticles of metal or liposomal origin, or as a primary miRNA by itself or conjugated to nanoparticles of metal or liposomal origin or delivered on a virus, or as a liposome, or as a polymer, or as a gene that is encoded by a nucleic acid and such nucleic acid is located on a vector, or as a gene is encoded by a nucleic acid, or as a precursor hairpin by itself or conjugated to nanoparticles of metal or liposomal origin.

Another preferred embodiment of the present invention discloses that such nucleic acid is located on a vector selected from the group consisting of a plasmid, cosmid, phagemid, virus, and other vehicles derived from viral or bacterial sources, or is located on a vector that may further comprise one or more in vivo expression elements selected from the group consisting of a promoter, enhancer, and combinations thereof.

Another preferred embodiment of the present invention relates to the use of miR-140-5p where the miRNA is administered to, or expression is increased in the cells of, a patient for treatment or prevention of cancer, including but not limited to neuroblastoma, lung cancer, pancreatic cancer, skin cancer, hematological neoplasms, breast cancer, brain cancer, colon cancer, follicular lymphoma, bladder cancer, cervical cancer, endometrial cancer, esophageal cancer, gastric cancer, head and neck cancer, multiple myeloma, liver cancer, lymphomas, oral cancer, osteosarcomas, ovarian cancer, prostate cancer, testicular cancer, and/or thyroid cancer.

Another preferred embodiment of the present invention relates to the use of miR-140-5p where miRNA is administered to, or expression is increased in the cells of, a patient for treatment or prevention of cancer and wherein the patient is undergoing one or more cancer therapies selected from the group consisting of surgery, chemotherapy, radiotherapy, thermotherapy, immunotherapy, hormone therapy and laser therapy.

Another embodiment of the present invention discloses a method for determining the sensitivity of a cancer to a miR-140-5p miRNA delivered on a suitable pharmaceutical carrier to bind to an mRNA encoded by an oncogene containing one or several miR-140-5p complementary site (LCS) in a cancerous or transformed cell or an organism with a cancerous or transformed cell; and determining if the cancerous or transformed cell growth or viability is inhibited or if expression of the oncogene is inhibited.

Modifications may be made to the sequence of a miRNA or a pre-miRNA without disrupting miRNA activity. As used herein, the term "functional variant" of a miRNA sequence refers to an oliginonucleotide sequence that varies from the natural miRNA sequence, but retains one or more functional characteristics of the miRNA (e.g. enhancement of cancer cell susceptibility to chemotherapeutic agents, cancer cell proliferation inhibition, induction of cancer cell apoptosis, specific miRNA target inhibition). In some embodiments, a functional variant of a miRNA sequence retains all of the functional characteristics of the miRNA. In certain embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99% identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the miRNA or precursor thereof under stringent hybridization conditions. Accordingly, in certain embodiments the nucleobase sequence of a functional variant may be capable of hybridizing to one or more target sequences of the miRNA.

In some embodiments, the complementary strand is modified so that a chemical group other than a phosphate or hydroxyl is at its 5' terminus. The presence of the 5' modification apparently eliminates uptake of the complementary strand and subsequently favors uptake of the active strand by the miRNA protein complex. The 5' modification can be any of a variety of molecules known in the art, including $NH_2$, $NHCOCH_3$, and biotin.

In another embodiment, the uptake of the complementary strand by the miRNA pathway is reduced by incorporating nucleotides with sugar modifications in the first 2-6 nucleotides of the complementary strand. It should be noted that such sugar modifications can be combined with the 5' terminal modifications described above to further enhance miRNA activities.

In some embodiments, the complementary strand is designed so that nucleotides in the 3' end of the complementary strand are not complementary to the active strand. This results in double-strand hybrid RNAs that are stable at the 3' end of the active strand but relatively unstable at the 5' end of the active strand. This difference in stability enhances the uptake of the active strand by the miRNA pathway, while reducing uptake of the complementary strand, thereby enhancing miRNA activity.

In some embodiments, miRNA sequences of the invention may be associated with a second RNA sequence that may be located on the same RNA molecule or on a separate RNA molecule as the miRNA sequence. In such cases, the miRNA sequence may be referred to as the active strand, while the encoded RNA sequence, which is at least partially complementary to the miRNA sequence, may be referred to as the complementary strand. The active and complementary strands may be hybridized to generate a double-stranded RNA that is similar to a naturally occurring miRNA precursor. The activity of a miRNA may be optimized by maximizing uptake of the active strand and minimizing uptake of the complementary strand by the miRNA protein complex that regulates gene translation. This can be done through modification and/or design of the complementary strand, for example.

miRNA used in the reaction may be obtained by a variety of methods and from a variety of sources. The miRNA may be obtained from a biological sample, such as a cell, tissue, or organ. It may be isolated from a biological sample that contains other RNA molecules as well, such as mRNA, tRNA, and/or rRNA. In certain instances, total RNA is first isolated from the sample and then the miRNA is separated from the other RNA, thereby enriching for miRNA. In some embodiments, the miRNA has been isolated away from other RNA to enrich for the miRNA, such that the miRNA substantially pure, meaning it is at least about 80%, 85%, 90%, 95% pure or more, but less than 100% pure, with respect to other RNA molecules. Alternatively, enrichment of miRNA may be expressed in terms of fold enrichment. In certain embodiments, miRNA is enriched by about, at least about, or at most about 5×, 10×, 20×, 30×, 40×, 50×, 60×, 70×, 80×, 90×, 100×, 250×, 500×, 1000×, and so forth. In some embodiments, the miRNA polynucleotide is synthesized.

MicroRNA molecules ("miRNAs") are generally 21 to 22 nucleotides in length, though lengths of 19 and up to 23 nucleotides have been reported. The miRNAs are each processed from a longer precursor RNA molecule ("precursor miRNA"). Precursor miRNAs are transcribed from non-protein-encoding genes. The precursor miRNAs have two regions of complementarity that enables them to form a stemloop- or fold-back-like structure, which is cleaved by an enzyme called Dicer in animals. Dicer is ribonuclease III-like nuclease. The processed miRNA is typically a portion of the stem. The processed miRNA (also referred to as "mature miRNA") becomes part of a large complex to down-regulate a particular target gene or genes. Examples of animal miRNAs include those that imperfectly basepair with the target, which halts translation (Olsen et al, 1999; Seggerson et al, 2002)

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled according to methods of the invention. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described Additional non-limiting examples of nucleosides, nucleotides or nucleic acids comprising 5-carbon sugar and/or backbone moiety derivatives or analogs, include the following, hereby incorporated by reference in their entireties:

U.S. Pat. No. 5,681,947, which describes oligonucleotides comprising purine derivatives that form triple helixes with and/or prevent expression of dsDNA;

U.S. Pat. Nos. 5,652,099 and 5,763,167, which describe nucleic acids incorporating fluorescent analogs of nucleosides found in DNA or RNA, particularly for use as fluorescent nucleic acids probes;

U.S. Pat. No. 5,614,617, which describes oligonucleotide analogs with substitutions on pyrimidine rings that possess enhanced nuclease stability;

U.S. Pat. Nos. 5,670,663, 5,872,232 and 5,859,221, which describe oligonucleotide analogs with modified 5-carbon sugars, i.e., modified 2'-deoxyfuranosyl moieties, used in nucleic acid detection;

U.S. Pat. No. 5,446,137, which describes oligonucleotides comprising at least one 5-carbon sugar moiety substituted at the 4' position with a substituent other than hydrogen that can be used in hybridization assays;

U.S. Pat. No. 5,886,165, which describes oligonucleotides with both deoxyribonucleotides with 3'-5' mternucleotide linkages and ribonucleotides with 2'-5' internucleotide linkages;

U.S. Pat. No. 5,714,606, which describes a modified internucleotide linkage wherein a 3'-position oxygen of the internucleotide linkage is replaced by a carbon to enhance the nuclease resistance of nucleic acids;

U.S. Pat. No. 5,672,697, which describes oligonucleotides containing one or more 5' methylene phosphonate mternucleotide linkages that enhance nuclease resistance;

U.S. Pat. Nos. 5,466,786 and 5,792,847, which describe the linkage of a substituent moiety which may comprise a drug or label to the 2' carbon of an oligonucleotide to provide enhanced nuclease stability and ability to deliver drugs or detection moieties;

U.S. Pat. No. 5,223,618, which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA;

U.S. Pat. No. 5,470,967, which describes oligonucleotides comprising at least one sulfamate or sulfamide internucleotide linkage that are useful as nucleic acid hybridization probe;

U.S. Pat. Nos. 5,378,825, 5,777,092, 5,623,070, 5,610,289 and 5,602,240, which describe oligonucleotides with three or four atom linker moiety replacing phosphodiester backbone moiety used for improved nuclease resistance, cellular uptake and regulating RNA expression;

U.S. Pat. No. 5,858,988, which describes hydrophobic carrier agent attached to the 2'-O position of oligonucleotides to enhanced their membrane permeability and stability;

U.S. Pat. No. 5,214,136, which describes oligonucleotides conjugated to anthraqumone at the 5' terminus that possess enhanced hybridization to DNA or RNA, enhanced stability to nucleases;

U.S. Pat. No. 5,700,922, which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154, which describes RNA linked to a DNA to form a DNA-RNA hybrid, and U.S. Pat. No. 5,728,525, which describes the labeling of nucleoside analogs with a universal fluorescent label.

Additional teachings for nucleoside analogs and nucleic acid analogs are:

U.S. Pat. No. 5,728,525, which describes nucleoside analogs that are end-labeled;

U.S. Pat. Nos. 5,637,683, 6,251,666 (L-nucleotide substitutions); and

U.S. Pat. No. 5,480,980 (7-deaza-2' deoxyguanosine nucleotides and nucleic acid analogs thereof).

Labeling methods and kits of the invention specifically contemplate the use of nucleotides that are both modified for attachment of a label and can be incorporated into an miRNA molecule. Such nucleotides include those that can be labeled with a dye, including a fluorescent dye, or with a molecule such as biotin. Labeled nucleotides are readily available; they can be acquired commercially or they can be synthesized by reactions known to those of skill in the art.

Modified nucleotides for use in the invention are not naturally occurring nucleotides, but instead, refer to prepared nucleotides that have a reactive moiety on them. Specific reactive functionalities of interest include: ammo, sulfhydryl, sulfoxyl, ammosulfhydryl, azido, epoxide, isothiocyanate, isocyanate, anhydride, monochlorotrazme, dichlorotrazme, mono- or dihalogen substituted pyridine, mono- or disubstituted diazme, maleimide, epoxide, aziudme, sulfonyl halide, acid hahde, alkyl hahde, aryl hahde, alkylsulfonate, N-hydroxysuccimmide ester, imido ester, hydrazine, azidomtro-phenyl, azide, 3-(2-pyridyl dithio)-propionarmde, glyoxal, aldehyde, Iodoacetyl, cyanomethyl ester, p-nitrophenyl ester, o-mtrophenyl ester, hydroxypyridme ester, carbonyl imidazole, and the other such chemical groups. In some embodiments, the reactive functionality may be bonded directly to a nucleotide, or it may be bonded to the nucleotide through a linking group. The functional moiety and any linker cannot substantially impair the ability of the nucleotide to be added to the miRNA or to be labeled.

Representative linking groups include carbon containing linking groups, typically ranging from about 2 to 18, usually from about 2 to 8 carbon atoms, where the carbon containing linking groups may or may not include one or more heteroatoms, e.g. S, O, N etc., and may or may not include one or more sites of unsaturation. Of interest in many embodiments are alkyl linking groups, typically lower alkyl linking groups of 1 to 16, usually 1 to 4 carbon atoms, where the linking groups may include one or more sites of unsaturation. The functionalized nucleotides or primers used in the above methods of functionalized target generation may be fabricated using known protocols or purchased from commercial vendors, e.g., Sigma, Roche, Ambion, and NEN. Functional groups may be prepared according to ways known to those of skill in the art, including the representative information found in U.S. Pat. Nos. 4,404,289; 4,405,711; 4,337,063, 5,268,486 and Br. Pat. No. 1,529,202.

Amine-modified nucleotides are used in several embodiments of the invention. The amine-modified nucleotide is a nucleotide that has a reactive amine group for attachment of the label. It is contemplated that any ribonucleotide (G, A, U, or C) or deoxyribonucleotide (G, A, T, or C) can be modified for labeling. Examples include, but are not limited to, the following modified ribo- and deoxyribo-nucleotides: 5-(3-aminoalryl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-tø-(ethylamine)]-CTP; N6-(6-Amino)hexyl-ATP; 8-[(6-Amino)hexyl]-amino-ATP; 5-propargylamino-CTP, 5-propargylamino-UTP; 5-(3-aminoallyl)-dUTP; 8-[(4-amino)butyl]-amino-dATP and 8-[(6-amino)butyl]-amino-dATP; N6-(4-amino)butyl-dATP, N6-(6-amino)butyl-dATP, N4-[2,2-oxy-bis-(ethylamine)]-dCTP; N6-(6-Amino)hexyl-dATP; 8-[(6-Amino)hexyl]-amino-dATP; 5-propargylamino-dCTP, and 5-propargylamino-dUTP. Such nucleotides can be prepared according to methods known to those of skill in the art. Moreover, a person of ordinary skill in the art could prepare other nucleotide entities with the same amine-modification, such as a 5-(3-aminoallyl)-CTP, GTP, ATP, dCTP, dGTP, dTTP, or dUTP in place of a 5-(3-aminoallyl)-UTP.

A nucleic acid may be made by any technique known to one of ordinary skill in the art, such as for example, chemical synthesis, enzymatic production or biological production. In some embodiments, miRNA compositions of the invention are chemically synthesized. In some embodiments of the invention, miRNAs are recovered from a biological sample. The miRNA may be recombinant or it may be natural or endogenous to the cell, that is produced from the cell's genome. It is contemplated that a biological sample may be treated in a way so as to enhance the recovery of small RNA molecules such as miRNA. Generally, methods involve lysing cells with a solution having guanidinium and a detergent.

Alternatively, nucleic acid synthesis is performed according to standard methods. Additionally, U.S. Pat. Nos. 4,704,362, 5,221,619, and 5,583,013 each describe various methods of preparing synthetic nucleic acids. Non-limiting examples of a synthetic nucleic acid, e.g., a synthetic oligonucleotide, include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al. (37) and U.S. Pat. No. 5,705,629. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, and 5,602,244.

A non-limiting example of an enzymatically produced nucleic acid include one produced by enzymes in amplification reactions such as PCR™ (see for example, U.S. Pat. No. 4,683,202 and U.S. Pat. No. 4,682,195), or the synthesis of an oligonucleotide described in U.S. Pat. No. 5,645,897. A non-limiting example of a biologically produced nucleic acid includes a recombinant nucleic acid produced, i.e., replicated, in a living cell, such as a recombinant DNA vector replicated in bacteria (see for example, Sambrook et al. Molecular Cloning: A Laboratory Manual. Cold Spring Harbor Laboratory, Cold Spring Harbor, N.Y., 1989). Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244.

Basically, chemical synthesis can be achieved by the diester method, the triester method polynucleotides phosphorylase method and by solid-phase chemistry. The diester method was developed to a usable state, primarily by Khorana and co-workers (38). The basic step is the joining of two suitably protected deoxynucleotides to form a dideoxynucleotide containing a phosphodiester bond. The diester method is well established and has been used to synthesize DNA molecules. The main difference between the diester and triester methods is the presence, in the latter of an extra protecting group on the phosphate atoms of the reactants and products. The phosphate protecting group is usually a chlorophenyl group, which renders the nucleotides and polynucleotide intermediates soluble in organic solvents. Therefore purification's are done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

The polynucleotide phosphorylase method is an enzymatic method of DNA synthesis that can be used to synthesize many useful oligonucleotides (39-40). Under controlled conditions, polynucleotide phosphorylase adds predominantly a single nucleotide to a short oligonucleotide. Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic nucleic acid synthesizers.

Phosphoramidite chemistry (41) is a widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain, that are anchored generally at one end to a suitable solid support, to form the oligonucleotide product.

Recombinant methods for producing nucleic acids in a cell are well known to those of skill in the art. These include the use of both viral and non-viral vectors, plasmids, cosmids, and other vehicles for delivering a nucleic acid to a cell, which may be the target cell or simply a host cell to produce large quantities of the desired RNA molecule. Alternatively, such vehicles can be used in the context of a cell free system so long as the reagents for generating the RNA molecule are present. Such methods include those described in Sambrook, 1989 and later editions.

In certain embodiments, the present invention concerns nucleic acid molecules that are not synthetic. In some embodiments, the nucleic acid molecule has a chemical structure of a naturally occurring nucleic acid and a sequence of a naturally occurring nucleic acid, such as the exact and entire sequence of a single stranded primary miRNA (22), a single-stranded precursor miRNA, or a single-stranded mature miRNA. In addition to the use of recombinant technology, such non-synthetic nucleic acids may be generated chemically, such as by employing technology used for creating oligonucleotides.

Thus, the present invention relates to the design, synthesis, construction, composition, characterization and use of microRNAs in treating cancer. More specifically, the invention discloses that artificial microRNA 140-5p is a potent tumor suppressor able to significantly suppress cell proliferation, increase apoptosis, suppress tumor growth and has the potential to increase sensitivity of chemotherapeutic drugs as illustrated from the clinical outcomes data presented in Example 4 when presented in the form of pri-miRNA, pre-miRNA, mature miRNA or fragments of variants thereof that retain the biological activity of the mature miRNA and DNA encoding a pri-miRNA, pre-miRNA, mature miRNA, fragments or variants thereof, or regulatory elements of the miRNA.

Another embodiment of the present invention discloses the use of miR-140-5p as a tumor suppressor of neuroblastoma that is repressed under conditions high levels of MYCN. As shown in the last panel from the top miR-140-5p and its host genes is significantly repressed under MYCN induction. miR-140-5p and its host gene is expressed at a reasonable level under low MYCN conditions.

A preferred embodiment of the present invention discloses that miR-140-5p significantly decreases the proliferation of the nueroblastoma cell line CHLA255 and significantly suppresses in vivo tumor growth and burden in an orthotopic xenograft mouse model of neuroblastoma. This is a common characteristic of tumor suppressor genes and microRNAs. From this work a person having ordinary skill in this art would readily conclude that miR-140-5p is a strong suppressor of neuroblastoma and other cancers.

Another preferred embodiment of the present invention teaches that miR-140-5p increases sensitivity to drugs commonly used to treat neuroblastoma and other cancers. Two improvements anticipated that patients able to respond to current doses of chemotherapy can be treated with much lower doses of chemotherapy when presented with miR-140-5p. More importantly, patients that do not respond to chemotherapy, or patients that respond but relapse, can be treated with regular doses of chemotherapy in presence of miR-140-5p.

Another preferred embodiment of the invention discloses the use of a nucleic acid construct encoding an artificial miRNA presented as a double-stranded RNA or precursor a hairpin or a primary miRNA in the single straded RNA form or encoded in a DNA vector delivered in a suitable pharmaceutical carrier, to be used for inhibiting the expression of all oncogenes and regulators of oncogenes containing a miR-140-5 p complementary site (LCS). The pharmaceutical carrier includes, but is not limited to, a virus, a liposome, or a polymer, and any combination thereof.

Another preferred embodiment of the present invention discloses the composition, methods and use of a nucleic acid construct encoding an artificial miRNA presented as a double-stranded RNA or precursor a hairpin or a primary miRNA in the single stranded RNA form or encoded in a DNA vector delivered in a suitable pharmaceutical carrier, to be used for inhibiting the expression of all oncogenes and regulators of oncogenes containing a miR-140-5p complementary site (LCS), wherein the miR-140-5p is delivered in multiple ways, to include but not limited to, as a mature miRNA by itself, or as a gene is encoded by a nucleic acid, or as a precursor hairpin by itself or conjugated to nanoparticles of metal or liposomal origin, or conjugated to nanoparticles of metal or liposomal origin, or as a primary miRNA by itself or conjugated to nanoparticles of metal or liposomal origin or delivered on a virus, or as a liposome, or as a polymer, or as a gene that is encoded by a nucleic acid and such nucleic acid is located on a vector, or as a gene is encoded by a nucleic acid, or as a precursor hairpin by itself or conjugated to nanoparticles of metal or liposomal origin.

Another preferred embodiment of the present invention discloses that such nucleic acid is located on a vector selected from the group consisting of a plasmid, cosmid, phagemid, virus, and other vehicles derived from viral or bacterial sources, or is located on a vector that may further comprises one or more in vivo expression elements selected from the group consisting of a promoter, enhancer, and combinations thereof.

Another preferred embodiment of the present invention relates to the use of miR-140-5p where miRNA is administered to, or expression is increased in the cells of, a patient for treatment or prevention of cancer, including but not limited to neuroblastoma, osteosarcoma, glioblastoma, lung cancer, pancreatic cancer, skin cancer, hematological neoplasms, breast cancer, brain cancer, colon cancer, follicular lymphoma, bladder cancer, cervical cancer, endometrial cancer, esophageal cancer, gastric cancer, head and neck cancer, multiple myeloma, liver cancer, lymphomas, oral cancer, osteosarcomas, ovarian cancer, uterine leiomyosarcoma, uterine leiomyomas, endometriomas, endometriosis, uterine papillary serous carcinomas, prostate cancer, testicular cancer, and/or thyroid cancer.

Another preferred embodiment of the present invention relates to the use of miR-140-5p where miRNA is administered to, or expression is increased in the cells of, a patient for treatment or prevention of cancer and wherein the patient is undergoing one or more cancer therapies selected from the group consisting of surgery, chemotherapy, radiotherapy, thermotherapy, immunotherapy, hormone therapy and laser therapy. More specifically, therapies include but are not limited to 13-cis-retinoic acid, antibodies, cytokines such as GM-CSF and IL-2, platinum compounds such as carboplatin, cisplatin, an alkylating agent such as cyclphosphamide or melphalan, an antimetabolite, an antitumor antibiotic or anthracycline antiobiotics such as doxorubicin, vinca alkaloids such as vincristine and a DNA topoisomerase inhibitor such as topeotecan or etoposide.

Another embodiment of the present invention discloses a method for determining the sensitivity of a cancer to a miR-140-5p miRNA delivered on a suitable pharmaceutical carrier to bind to an mRNA encoded by an oncogene containing one or several miR-140-5p complementary site (LCS) in a cancerous or transformed cell or an organism with a cancerous or transformed cell; and determining if the cancerous or transformed cell growth or viability is inhibited or if expression of the oncogene is inhibited.

Method of Administration

In general, methods of administering nucleic acids are well known in the art. In particular, the routes of administration already in use for nucleic acid therapeutics, along with formulations in current use, provide preferred routes of administration and formulation for the nucleic acids. Nucleic acid compositions can be administered by a number of routes including, but not limited to: oral, intravenous, intraperitoneal, intramuscular, transdermal, subcutaneous, topical, sublingual, or rectal means. Nucleic acids can also be administered via liposomes or nanoparticles. Such administration routes and appropriate formulations are generally known to those of skill in the art. Administration of the formulations described herein may be accomplished by any acceptable method that allows the miRNA or nucleic acid encoding the miRNA to reach its target. The particular mode selected will depend of course, upon exemplary factors such as the particular formulation, the severity of the state of the subject being treated, and the dosage required for therapeutic efficacy. As generally used herein, an "effective amount" of a nucleic acid is the amount that is able to treat one or more symptoms of cancer or related disease, reverse the progression of one or more symptoms of cancer or related disease, halt the progression of one or more symptoms of cancer or related disease, or prevent the occurrence of one or more symptoms of cancer or related disease in a subject to whom the formulation is administered, as compared to a matched subject not receiving the compound or therapeutic agent. The actual effective amounts of drug can vary according to the specific drug or combination thereof being utilized, the particular composition formulated, the mode of administration, and the age, weight, condition of the patient, and severity of the symptoms or condition being treated.

Any acceptable method known to one of ordinary skill in the art may be used to administer a formulation to the subject. The administration may be localized, that is, to a particular region, physiological system, tissue, organ, or cell type, or systemic, depending on the condition being treated. Injections can be, for example, intravenous, intradermal, subcutaneous, intramuscular, or intraperitoneal. The composition can be injected intradermally for treatment or prevention of cancer, for example. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the composition with an aerosol in an inhaler, either alone or attached to a carrier that can be absorbed. For systemic administration, it may be preferred that the composition is encapsulated in liposomes.

Preferably, the agent and/or nucleic acid delivery system are provided in a manner that enables tissue-specific uptake of the agent and/or nucleic acid delivery system. Techniques include using tissue or organ localizing devices, such as wound dressings or transdermal delivery systems, using invasive devices such as vascular or urinary catheters, and using interventional devices such as stents having drug delivery capability and configured as expansive devices or stent grafts. The formulations may be delivered using a bioerodible implant by way of diffusion or by degradation of the polymeric matrix. In certain embodiments, the administration of the formulation may be designed so as to result in sequential exposures to the miRNA over a certain time period, for example, hours, days, weeks, months or years. This may be accomplished, for example, by repeated administrations of a formulation or by a sustained or controlled release delivery system in which the miRNA is delivered over a prolonged period without repeated administrations. Administration of the formulations using such a delivery system may be, for example, by oral dosage forms, bolus injections, transdermal patches or subcutaneous implants. Maintaining a substantially constant concentration of the composition may be preferred in some cases.

Other delivery systems suitable include, but are not limited to, time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing nucleic acids are described in, for example, U.S. Pat. No. 5,075,109.

Other examples include nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include, but are not limited to, erosional systems in which the miRNA is contained in a formulation within a matrix (for example, as described in U.S. Pat. Nos. 4,452,775, 4,675,189, 5,736,152, 4,667,013, 4,748,034 and 5,239,660), or diffusional systems in which an active component controls the release rate (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the miRNA. In addition, a pump-based hardware delivery system may be used to deliver one or more embodiments.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be, e.g., in the form of pellets, or capsules. Use of a long-term release implant may be particularly suitable in some embodiments. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

Dosages for a particular patient can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose-administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the miRNA employed and the condition of the patient, as well as the body weight or surface area of the patient to be treated. The size of the dose is also determined by the existence, nature, and extent of any adverse side-effects that accompany the administration of a particular vector, and formulation, in a particular patient.

Therapeutic compositions comprising one or more nucleic acids are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of treatment versus non-treatment (e.g., comparison of treated vs. untreated cells or animal models), in a relevant assay. Formulations are administered at a rate determined by the LD50 of the relevant formulation, and/or observation of any side-effects of the nucleic acids at various concentrations, e.g., as applied to the mass and overall health of the patient. Administration may be via single or divided doses.

In determining the effective amount of the miRNA to be administered in the treatment or prophylaxis of disease the physician evaluates circulating plasma levels, formulation toxicities, and progression of the disease. The dose administered to a 70 kilogram patient is typically in the range equivalent to dosages of currently-used therapeutic antisense oligonucleotides such as Vitravene® (fomivirsen sodium injection) which is approved by the FDA for treatment of cytomegaloviral RNA, adjusted for the altered activity or serum half-life of the relevant composition.

The formulations described herein can supplement treatment conditions by any known conventional therapy, including, but not limited to, antibody administration, vaccine administration, administration of cytotoxic agents, natural amino acid polypeptides, nucleic acids, nucleotide analogues, and biologic response modifiers. Two or more combined compounds may be used together or sequentially. For example, the nucleic acids can also be administered in therapeutically effective amounts as a portion of an anti-cancer cocktail. An anti-cancer cocktail is a mixture of the oligonucleotide or modulator with one or more anti-cancer drugs in addition to a pharmaceutically acceptable carrier for delivery. The use of anti-cancer cocktails as a cancer treatment is routine.

Anti-cancer drugs that are well known in the art and can be used as a treatment in combination with the nucleic acids described herein include, but are not limited to: actinomycin D, aminoglutethimide, asparaginase, bleomycin, busulfan, carboplatin, carmustine, chlorambucil, cisplatin (cis-DDP), cyclophosphamide, cytarabine HCl (cytosine arabinoside), dacarbazine, factinomycin, daunorubicin HCl, doxorubicin HCl, Estramustine phosphate sodium, rtoposide (V16-213), floxuridine, 5-fluorouracil (5-Fu), flutamide, hydroxyurea (hydroxycarbamide), Ifosfamide, Interferon apha-2a, interferon alpha-2b, leuprolide acetate (LHRH-releasing factor analog), lomustine, mechlorethamine HCl (nitrogen mustard), melphalan, mercaptopurine, mesna, methotrexate (MTX), mitomycin, mitoxantrone hcl, octreotide, plicamycin, procarbazine hcl, streptozocin, tamoxifen citrate, thioguanine, thiotepa, vinblastine sulfate, vincristine sulfate, amsacrine, azacitidine, hexamethylmelamine, interleukin-2, mitoguazone, pentostatin, semustine, teniposide, and vindesine sulfate.

Chemotherapeutic Agents

These can be, for example, agents that directly cross-link DNA, agents that intercalate into DNA, and agents that lead to chromosomal and mitotic aberrations by affecting nucleic acid synthesis. Agents that directly cross-link nucleic acids, specifically DNA, are envisaged and are shown herein, to eventuate DNA damage leading to a synergistic antineoplastic combination. Agents such as cisplatin, and other DNA alkylating agents may be used. Agents that damage DNA also include compounds that interfere with DNA replication, mitosis, and chromosomal segregation. Examples of these compounds include adriamycin (also known as doxorubicin), VP-16, also known as etoposide, verapamil, podophyllotoxin, and the like. Widely used for the treatment of neoplasms, these compounds are administered through bolus injections intravenously at doses ranging from 25-75 mg/m$^2$ at 21 day intervals for adriamycin, to 35-100 mg/m$^2$ for etoposide intravenously or orally.

Exemplary chemotherapeutics include at least 1) antibiotics, such as doxorubicin, daunorubicin, mitomycin, Actinomycin D; 2) platinum-based agents, such as cisplatin; 3) plant alkaloids, such as taxol and vincristine, vinblastine; 4) alkylating agents, such as carmustine, melphalin, cyclophosphamide, chlorambucil, bisufan, an dlomustine.

In some embodiments of the invention, one or more microRNAs are employed to enhance immunotherapy cancer treatment in an individual. In specific aspects, the immunotherapy comprises monoclonal antibodies. In some embodiments of the invention, one or more microRNAs are employed to enhance hormone therapy cancer treatment in an individual. Hormone therapy is a form of systemic therapy that is most often used to help reduce the risk of the cancer coming back after surgery, but it may also be used for cancer that has spread or come back after treatment. The therapy may include drugs to block hormones or drugs that change hormone levels.

Pharmaceutical compositions of the present invention comprise an effective amount of one or more microRNAs dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one microRNA or additional active ingredient will be known to those of skill in the art in light of the present disclosure, as exemplified by Remington's Pharmaceutical Sciences, 18th Ed. Mack Printing Company, 1990. Moreover, for non-human animal or human administration, preparations should meet sterility, pyrogenicity, general safety and purity standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329).

The microRNA may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990).

The microRNA may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens, e.g., methylparabens and propylparabens, chlorobutanol, phenol, sorbic acid, thimerosal or combinations thereof. In accordance with the present invention, the composition is combined with the carrier in any convenient and practical manner, i.e., by solution, suspension, emulsification, admixture, encapsulation, absorption and the like.

In further embodiments, the present invention may concern the use of a pharmaceutical lipid vehicle compositions that include microRNA, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic. However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the microRNA may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In preferred embodiments of the present invention, the microRNA are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like, as in U.S. Pat. Nos. 5,641, 515; 5,580,579 and 5,792,451. The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.

When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Gelatin capsules, tablets, or pills may be enterically coated. Enteric coatings prevent denaturation of the composition in the stomach or upper bowel where the pH is acidic, as in, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells.

A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. As another alternative, the compositions may be fashioned into a tablet or solution form that may be placed under the tongue or otherwise dissolved in the mouth. Additional formulations which are suitable for other modes of alimentary administration include suppositories.

In further embodiments, microRNA may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641,515; and 5,399,363.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions, e.g., U.S. Pat. No. 5,466,468. In all cases the form must be sterile and must be fluid to the extent that easy injectability exists. It must be stable under the conditions of manufacture and storage and must be preserved against the contaminating action of microorganisms, such as bacteria and fungi.

The carrier can be a solvent or dispersion medium containing, for example, water, ethanol, polyol, i.e., glycerol, propylene glycol, and liquid polyethylene glycol, and the like, suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In other preferred embodiments of the invention, the active compound microRNA may be formulated for administration via various miscellaneous routes, for example, topical, e.g., transdermal, administration, mucosal administration, such as intranasal, vaginal, etc., and/or inhalation. Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only.

Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212. Likewise, the delivery of drugs using intranasal microparticle resins and lysophosphatidyl-glycerol compounds (U.S. Pat. No. 5,725,871) are also well-known in the pharmaceutical arts. Likewise, transmucosal drug delivery in the form of a polytetrafluoroetheylene support matrix is described in U.S. Pat. No. 5,780,045.

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Kits are also included as part of the invention. Kits for implementing methods of the invention described herein are specifically contemplated. In some embodiments, there are kits for treating and/or preventing cancer. In some embodiments, the kit comprises one or more miR-140-5p and optionally a cancer treatment. In some embodiments, kit comprises in suitable container means, one or more of the following: 1) poly(A) polymerase; 2) nucleotides (G, A, T, C, and/or U); 3) poly(A) polymerase buffer; reaction buffer; 4) solutions for preparing, isolating, enriching, and/or purifying miRNAs. Other reagents include those generally used for manipulating RNA, such as formamide, loading dye, ribonuclease inhibitors, and DNase. Pharmaceutical carriers for the microRNA composition may or may not be included in the kit.

Although in some embodiments the kit comprises the microRNA composition, in other embodiments the microRNA composition is synthesized. Poly(A) polymerase may be from any source, but specifically contemplated is a poly(A) polymerase from yeast or *E. coli*, which may be recombinant or purified from the organism. A reaction buffer for poly(A) polymerase may be included in any kit of the invention. Typically, such a poly(A) polymerase reaction buffer includes a volume exclusion reagent, such as PEG, magnesium, and sodium.

In certain embodiments, the poly(A) polymerase reaction buffer in the kit contains at least: about 5, 6, 7, 8, 9, 10, 11, 12, 13, 14, 15% or more (or any range derivable therein) PEG; about 5, 10, 15, 20, 25, 30, 35, 40, 45, 50 mM or more $MgCl_2$ (or any range derivable therein); about 100, 200, 300, 400, 500, 600, 700, 800, 900 mM NaCl (or any range derivable therein); about 50, 60, 70, 80, 90, 100, 110, 120, 130, 140, 150 mM or more MES (or any range derivable therein); and about 0.5, 1, 1.5, 2, 2.5, 3, 3.5, 4 mM or more DTT or any range derivable therein. The kits may also include a manganese source, which may be included as a separate component of a kit or in a solution or buffer with other components, such as in the reaction buffer. It is contemplated that about 5, 10, 15, 20, 25, 30, 35, 40, 45, 50 mM or more of $MnCl_2$ is included in the kit Nucleotides may also be included in kits of the invention. Nucleotides may be for DNA or RNA. Concentrations of a nucleotide or of a nucleotide mix, i.e., total concentration of all nucleotides, include, but are not limited to, about, at least about, or at most about 0.5, 1.0, 1 5, 2 0, 2.5, 3.0, 3.5, 4.0, 4.5, 5.0, 5 5, 6.0, 6.5, 7 0, 7.5, 8 0, 8 5, 90, 9 5, 10 0 mM or more or any range derivable therein. Moreover, they may be modified or not modified. If they are modified, they may have a reactive group or they may have a label attached to it. In certain embodiments, one or more nucleotides in a kit has a reactive group, such as an amine-reactive group.

In other embodiments, a nucleotide is already labeled. It may be labeled with a chemilummescent or fluorescent label, such as a dye. Specifically contemplated are amine-reactive dyes. Moreover, it is specifically contemplated that kits may or may not contain both modified and unmodified nucleotides. Also, kits may contain the label that will be attached to the nucleotide. Any label that can be attached to a nucleotide, as well as any specifically identified herein, can be included in kits of the invention.

Individual components may also be provided in a kit in concentrated amounts. In some embodiments, a component is provided individually in the same concentration as it would be in a solution with other components. Concentrations of components may be provided as 1×, 2×, 5×, 10×, or 20× or more. Any nucleic acid described herein may be implemented as part of a kit. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, for example, a labeling reagent and label may be packaged together, the kit also will contain generally a second, third or other additional container into which the additional components may be separately placed. However, various combinations of components may be comprised in a vial.

The kits of the present invention also typically will include a means for containing the nucleic acids and any other reagent containers in close confinement for commercial sale. Such containers may include injection or blow-molded plastic containers into which the desired vials are retained. When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

Such kits may also include components that facilitate isolation of the labeled miRNA. It may also include components that preserve or maintain the miRNA or that protect against its degradation. Such components may be RNAse-free or protect against RNAses. Such kits generally will comprise, in suitable means, distinct containers for each individual reagent or solution. A kit will also include instructions for employing the kit components as well the use of any other reagent not included in the kit. Instructions may include variations that can be implemented.

Kits of the invention may also include one or more of the following: Control RNA; nuclease-free water, RNase-free containers, such as 1.5 ml tubes; RNase-free elution tubes, PEG or dextran, ethanol; acetic acid, sodium acetate; ammonium acetate; guanidimum, detergent; nucleic acid size marker, RNase-free tube tips; and RNase or DNase inhibitors. It is contemplated that such reagents are embodiments of kits of the invention. Such kits, however, are not limited to the particular items identified above and may include any reagent used for the manipulation or characterization of miRNA. In some embodiments of the invention, additional anti-cancer agents are included in the kit. Examples include chemotherapeutics, hormone therapy agents, and immunotherapy agents.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1 microRNA-140-5p Suppresses Neuroblastoma

In FIG. 1 using a conditional MYCN cells line MYCN3, neuroblastoma patients with high and low MYCN were simulated. The MYCN3 cell line rapidly upregulated MYCN expression upon exposure to 1 ug/ml doxorubicin. QPCR for mRNA expression showed a 20-fold increase in message level with a concomitant increase in protein. Induced MYCN is functional as shown by alteration in cell cycle distribution 24 hours after exposure to doxorubicin. Chip-PCR results for E-boxes of two known MYCN target genes MIR17HG and MDM2 confirming the specificity of the immunoprecipitation and relative enrichment for MYCN target gene promoters. As shown in the last panel from the top miR-140-5p and its host genes is significantly repressed under MYCN induction. miR-140-5p and its host gene are expressed at a reasonable level under low MYCN conditions.

Example 2

Effect of microRNA-140-5p on CHLA255 Cells In Vitro hsa-microRNA-140-3p sequences (SEQ ID NOS: 3-4), which mimic miR-140-5p wildtype (SEQ ID NO: 1) and mutant miR-140-5p (SEQ ID NO: 2), were transfected into CHLA255 neuroblastoma cell line upper-GFP vector. Table 1 identifies the nucleotide sequences of the wildtype and mutant microRNAs and their mimics. The altered nucleotides in the mutant sequences are shown in bold.

TABLE 1

| MicroRNA | SEQUENCE | SEQUENCE ID |
| --- | --- | --- |
| microRNA-140-5p (wt) | CAGUGGUUUUACCCUAUGGUAG | SEQ ID NO: 1 |
| microRNA-140-5p (mut) | CCGGCGUUUUACCCUAUGGUAG | SEQ ID NO: 2 |
| hsa-microRNA-140-3p (wt) | UACCACAGGGUAGAACCACGG | SEQ ID NO: 3 |
| hsa-microRNA-140-3p (mut) | UACGACGCGGUAGAACCACGG | SEQ ID NO: 4 |

Figure 2A:
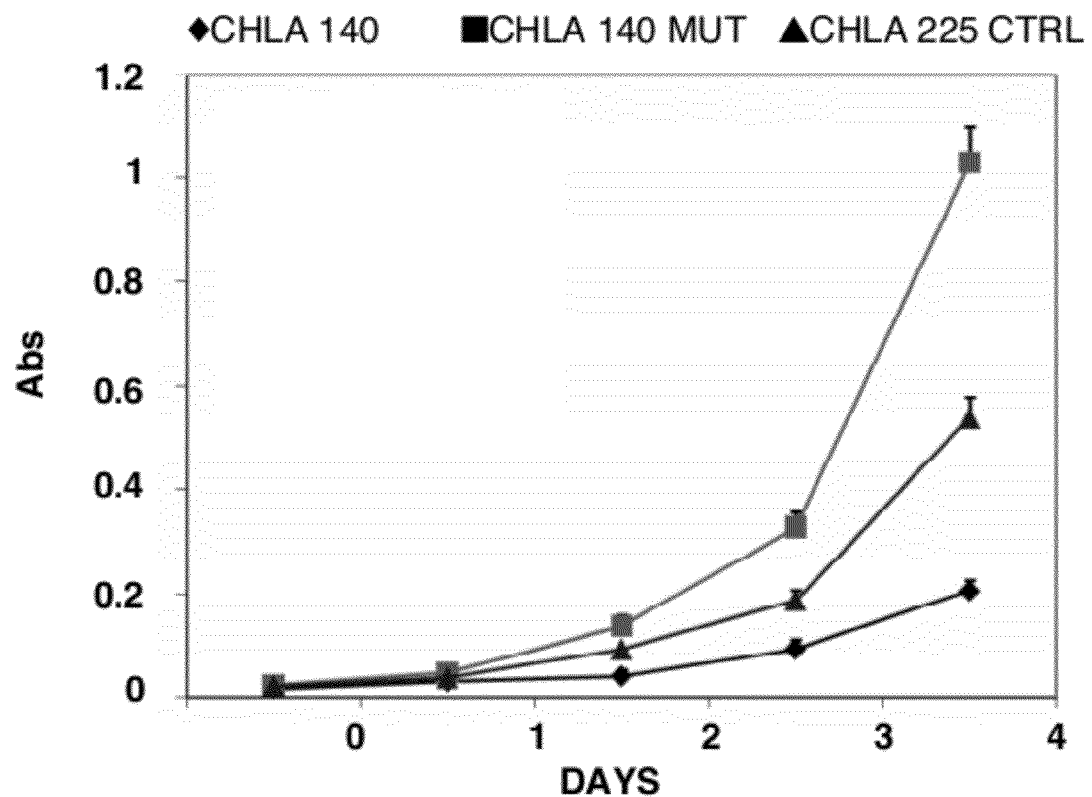
FIGS. 2A-2B are an in vitro evaluation of miR-140-5p on cell proliferation and clonogenicty of the neuroblastoma cell line CHLA255.
Figure 2B:
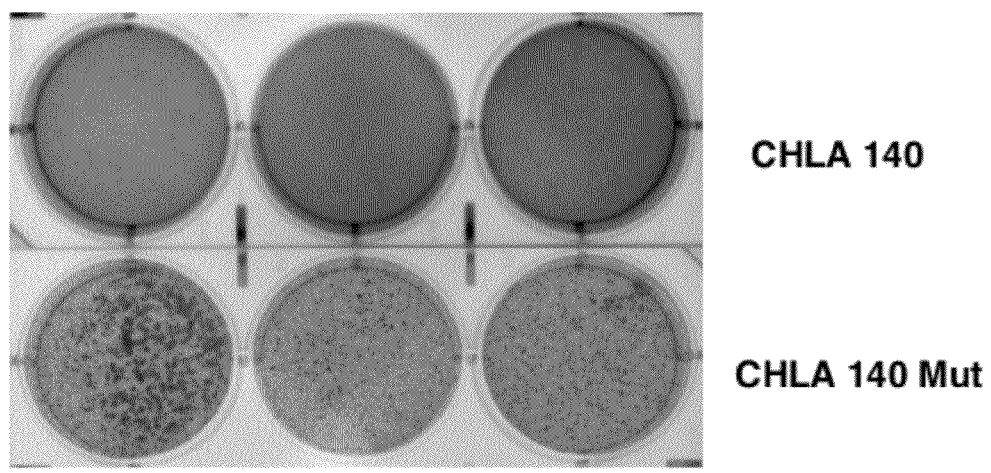

The impact of these sequences on these cells was measured by increase in absorbance from the MTT assay (FIG. 2A) and the ability to form colonies on a soft agar plate in a clonogenicity assay (FIG. 2B). Stable cell line expression of microRNAs with GFP were compared to control cells. Proliferation as measured by increase in absorbance from MTT assay. miR-140-5p was able to consistently decrease the proliferation rates of CHLA-255. Colony formation assays were carried out in soft agar-representative wells showing colony growth at 10 days. Colonies were stained and counted by eye or by digital image analysis software. Colony counts from triplicate experiments showed that miR-140-5p was able to significantly decrease colonies in CHLA255.

Example 3

Effect of microRNA-140-5p on Neuroblastoma In Vivo

Figure 3:
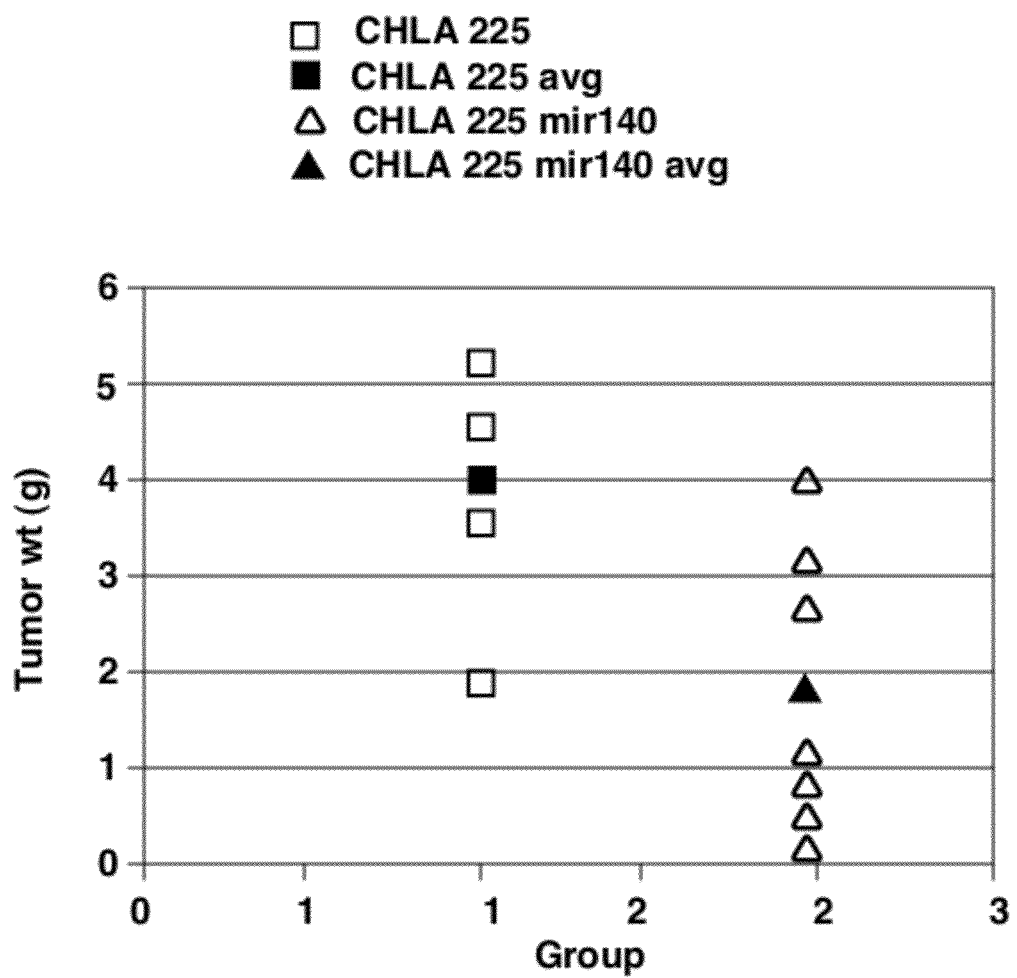
FIG. 3 illustrates the impact of miR-140-5p on in vivo orthotopic xenograft model of neuroblastoma. *Kruskal-Wallis method p<0.01; mean±SEM; n=9 in miR-140-5p cohort, n=10 in all other cohorts.

Using the contralateral kidney (*) for comparison the average tumor weight for each cohort+SEM. Tumors over-expressing miR-140-5p are significantly smaller than control CHLA-255 (FIG. 3).

Example 4

Figure 4A:
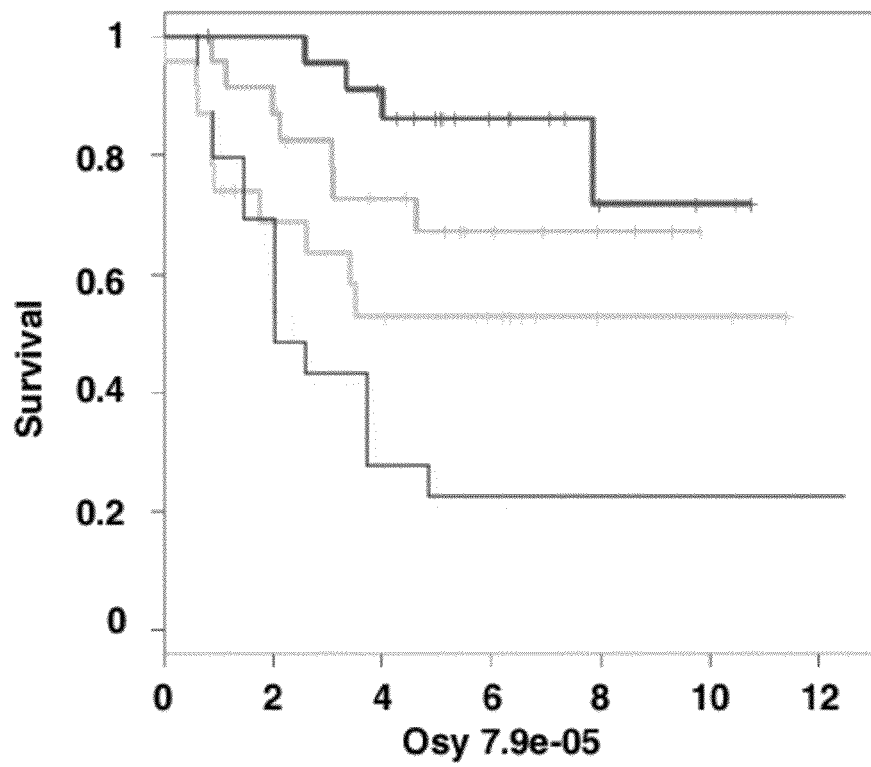
FIGS. 4A-4B depict correlations of microRNA host genes with expression with clinical outcome in neuroblastoma.
Figure 4B:
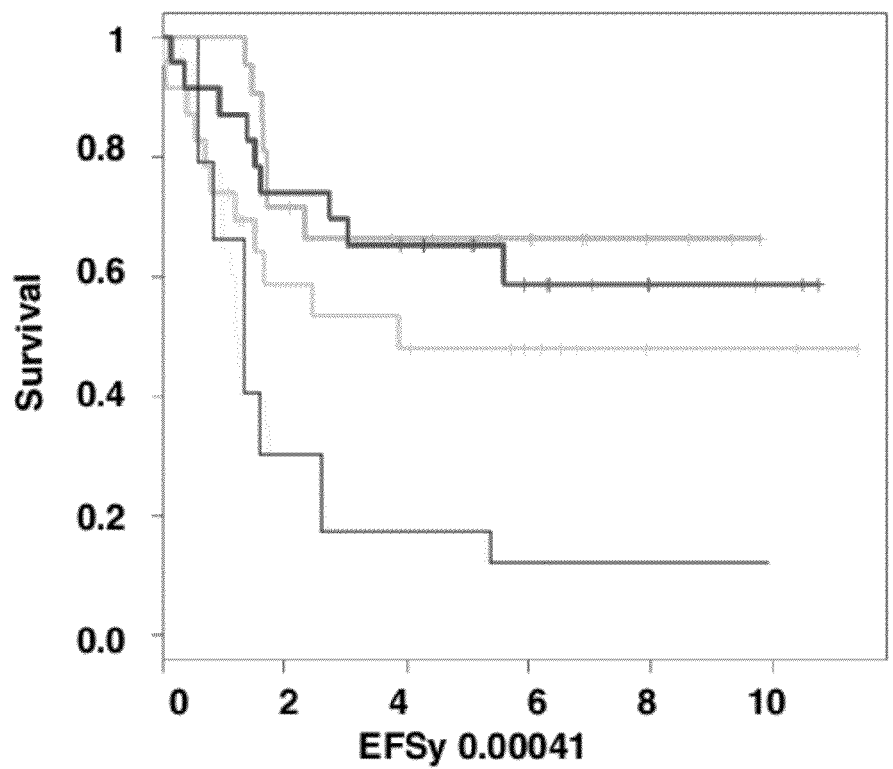

MicroRNA Host Genes Expression Correlates with Clinical Outcome of Neuroblastoma Representative Kaplan-Meier survival curves for illustrating both positive (higher expression=better outcome) and negative (lower expression=worse outcome) for miR-140-5p are shown in FIGS. 4A-4B. Survival probability and p-values calculated using Kaplan-Meier and Mantel-Haenszel methods as described previously (for log-rank testing, n=28 samples in each group). Overall, 50% of genes containing microRNAs had significant correlations when queried with this data set.

The following references are cited herein.
1. Fire et al. (1998) Nature 391:806-810.
2. Fire et al. (1999) Trends Genet. 15:358-363.
3. Bernstein et al. (2001) Nature 409:363-366.
4. Elbashir et al. (2001) Genes Dev 15:188-200.
5. Hutvagner et al. (2001) Science 293:834-838.
6. Allshire, Science (2002) 297:1818-1819.
7. Volpe et al. (2002) Science 297:1833-1837.
8. Jenuwein (2002) Science 297:2215-2218.
9. Hall et al. (2002) Science 297:2232-2237.
10. Wianny and Goetz ((1999) Nature Cell Biol 2:70.
11. Hammond et al. ((2000) Nature 404:293-296.
12. Lagos-Quintana et al. (2001) Science 294:853-858.
13. Lagos-Quintana et al. (2002) Curr Biol 12:735-739.
14. Lau et al. (2002) Science 294:858-862.
15. Lee and Ambros (2001) Science 294:862-864.
16. Llave et al. (2002) Plant Cell 14:1605-1619.
17. Mourelatos et al. (2002) Genes Dev 16:720-728.
18. Park et al. (2002) Curr Biol 12:1484-1495.
19. Reinhart et al. (2002) Genes Dev 16:1616-1626.
20. Grishok et al. (2001) Cell 106:23-34.
21. Ketting et al. (2001) Genes Dev 15:2654-2659.
22. Lee et al. (2002) EMBO J. 21:4663-4670.
23. Schwartz et al. (2003) Cell 115:199-208.
24. Lee et al. (1993) Cell 75:843-854.
25. Reinhart et al. (2000) Nature 403-901-906.
26. Guo et al. (2005) Plant Cell 17:1376-1386.
27. Wightman et al. (1993) Cell 75:855-862.
28. Slack et al. (2000) Mol Cell 5:659-669.
29. Olsen and Ambros (1999) Dev Biol 216:671-680.
30. Hutvagner and Zamore (2002) Science 297:2056-2060.
31. Hamilton and Baulcombe (1999) Science 286:950-952.
32. Zamore et al., (2000) Cell 31:25-33.
33. Elbashir et al., (2001) Nature 411:494-498.
34. Rhoades et al. (2002) Cell 110:513-520.
35. Buchman and Berg (1988) Mol Cell Biol 8:4395-4405.
36. Callis et al. (1987) Genes Dev 1:1183-1200.
37. Froehler et al. (1986) Nucleic Acids Research, 14(13): 5399-5407.
38. Khorana, H. G. (1979) Science 203:614.
39. Gillam et al. (1978) JBC 253:2532.
40. Gillam et al. (Feb. 16, 1979) Science 203(4381):614-25.
41. Beaucage and Lyer (1992) Tetrahedron 48:2223-2311.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention.

What is claimed is:

1. A method for improving a response to a therapy for neuroblastoma in a subject, comprising the step of:
   administering an effective amount of microRNA-140-5p to the subject.

2. The method of claim 1, wherein said microRNA-140-5p is administered as a nucleic acid construct encoding an artificial miRNA presented as a double-stranded RNA, a precursor hairpin, a primary miRNA in single stranded RNA form or encoded in a DNA vector delivered in a suitable pharmaceutical carrier.

3. The method of claim 1, wherein said therapy is one or more of surgery, chemotherapy, radiotherapy, thermotherapy, immunotherapy, hormone therapy, and laser therapy.

4. The method of claim 3, wherein said therapy is treatment with one or more of 13-cis-retinoic acid, an antibody, a cytokine, a platinum compound, an alkylating agent, an antimetabolite, vinca alkaloid, or a DNA topoisomerase inhibitor.

5. The method of claim 4, wherein said cytokine is GM-CSF, IL-2 or GM-CSF/IL-2.

6. The method of claim 4, wherein said platinum compound is carboplatin or cisplatin.

7. The method of claim 4, wherein said alkylating agent is cyclphosphamide or melphalan.

8. The method of claim 4, wherein said antimetabolite is an antitumor antibiotic or an anthracycline antiobiotic.

9. The method of claim 8, wherein said antibiotic is doxorubicin.

10. The method of claim 4, wherein said vinca alkaloid is vincristine.

11. The method of claim 4, wherein said DNA topoisomerase inhibitor is topeotecan or etoposide.

12. A method for treating neuroblastoma in a subject in need of such treatment comprising the step of:
    administering a pharmacologically effective amount of a pharmaceutical composition comprising microRNA-140 5p and a suitable pharmaceutical carrier to the subject.

13. The method of claim 12, wherein said agent is a double-stranded miRNA mimic or an oligonucleotide based pre-microRNA-140-5p drug.

14. The method of claim 12, wherein said microRNA-140-5p is administered as a nucleic acid construct encoding an artificial miRNA presented as a double-stranded RNA, a precursor hairpin, a primary miRNA in single stranded RNA form or encoded in a DNA vector delivered in the suitable pharmaceutical carrier.

15. The method of claim 12, wherein said pharmaceutical carrier is a virus, a liposome, or a polymer.

16. The method of claim 12, wherein said microRNA-140-5p is administered as a nanoparticle, a liposome, a vector or a polymer.

17. The method of claim 16, wherein said vector is a plasmid, a cosmid, a phagemid, or a virus.

18. The method of claim 12, further comprising:
treating said subject with one or more of a surgery, chemotherapy, radiotherapy, thermotherapy, immunotherapy, hormone therapy, or laser therapy.

19. The method of claim 18, wherein said treating step comprises treating with one or more of 13-cis-retinoic acid, an antibody, a cytokine, a platinum compound, an alkylating agent, an antimetabolite, vinca alkaloid, or a DNA topoisomerase inhibitor.

20. The method of claim 19, whereby said cytokine is GM-CSF, IL-2 or GM-CSF/IL-2.

21. The method of claim 19, wherein said platinum compound is carboplatin or cisplatin.

22. The method of claim 19, wherein said alkylating agent is cyclphosphamide or melphalan.

23. The method of claim 19, wherein said antimetabolite is an antitumor antibiotic or anthracycline antiobiotic.

24. The method of claim 23, wherein said antibiotic is doxorubicin.

25. The method of claim 19, wherein said vinca alkaloid is vincristine.

26. The method of claim 19, wherein said DNA topoisomerase inhibitor is topeotecan or etoposide.

* * * * *

SEQUENCE LISTING

```
<160> NUMBER OF SEQ ID NOS: 4

<210> SEQ ID NO 1
<211> LENGTH: 22
<212> TYPE: RNA
<213> ORGANISM: Artificial Sequence
<220> FEATURE:
<223> OTHER INFORMATION: Sequence of wildtype microRNA-140-5p

<400> SEQUENCE: 1
cagugguuuu acccuauggu ag                                          22

<210> SEQ ID NO 2
<211> LENGTH: 22
<212> TYPE: RNA
<213> ORGANISM: Artificial Sequence
<220> FEATURE:
<223> OTHER INFORMATION: Sequence of mutant microRNA-140-5p

<400> SEQUENCE: 2
ccggcguuuu acccuauggu ag                                          22

<210> SEQ ID NO 3
<211> LENGTH: 21
<212> TYPE: RNA
<213> ORGANISM: Artificial Sequence
<220> FEATURE:
<223> OTHER INFORMATION: Sequence of wildtype hsa-microRNA-140-3p

<400> SEQUENCE: 3
uaccacaggg uagaaccacg g                                           21

<210> SEQ ID NO 4
<211> LENGTH: 21
<212> TYPE: RNA
<213> ORGANISM: Artificial Sequence
<220> FEATURE:
<223> OTHER INFORMATION: Sequence of mutant hsa-micro-RNA140-3p

<400> SEQUENCE: 4
uacgacgcgg uagaaccacg g                                           21
```